Figure 1:
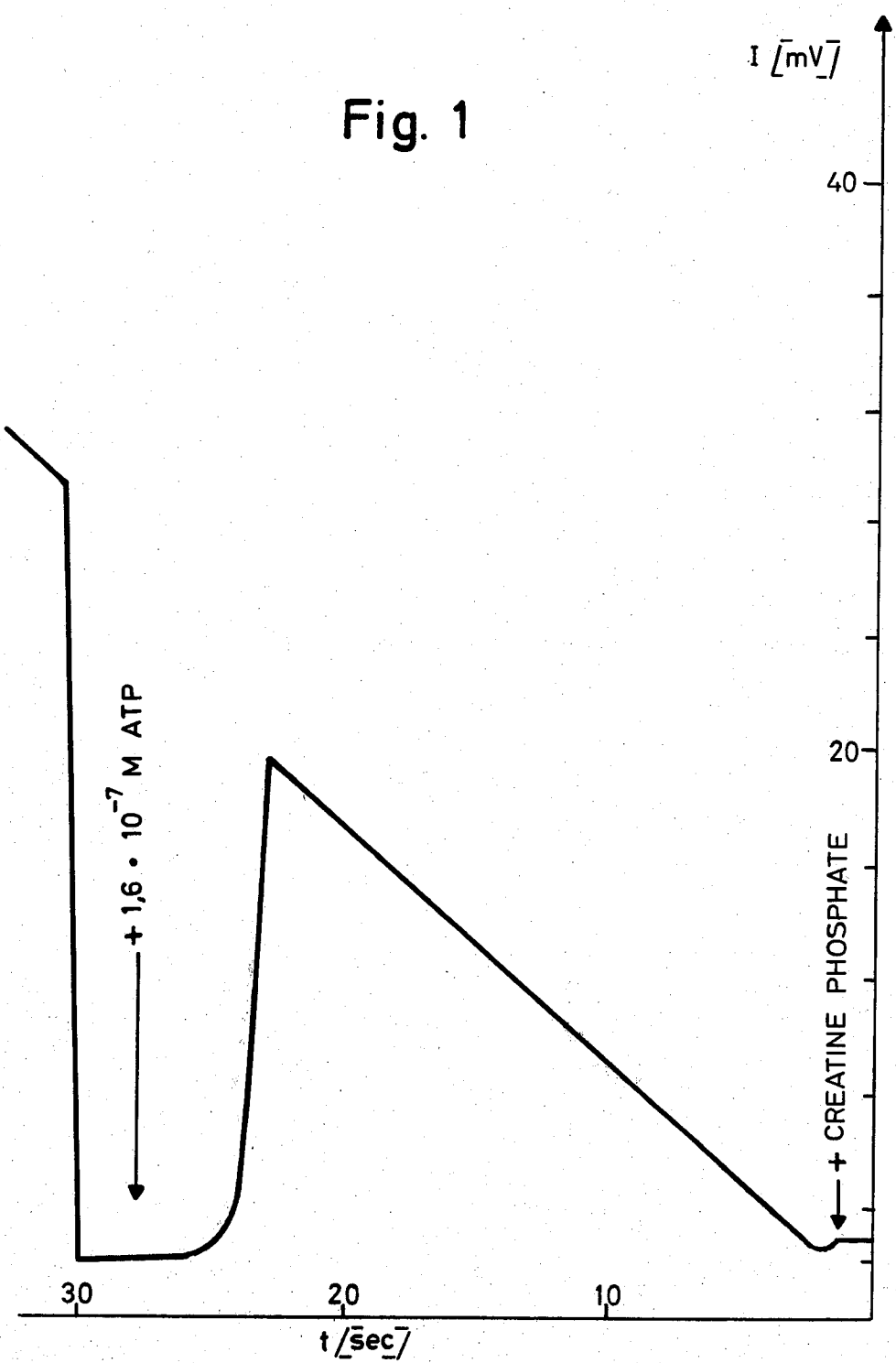

United States Patent [19]

Lundin

[11] 4,235,961
[45] Nov. 25, 1980

[54] METHOD FOR PHOTOMETRIC DETERMINATION OF THE SUBUNIT B OF CREATINE KINASE AND A REAGENT FOR CARRYING OUT THE METHOD

[75] Inventor: Arne T. Lundin, Stockholm, Sweden

[73] Assignee: LKB-Produkter AB, Bromma, Sweden

[21] Appl. No.: 50,518

[22] Filed: Jun. 21, 1979

[30] Foreign Application Priority Data

Jun. 29, 1978 [DE] Fed. Rep. of Germany ....... 2888658

[51] Int. Cl.$^3$ .............................................. C12Q 1/66
[52] U.S. Cl. ........................................ 435/8; 435/17; 435/184; 435/810
[58] Field of Search ...................... 435/8, 17, 184, 810; 424/2

[56] References Cited

U.S. PATENT DOCUMENTS

| | | | |
|---|---|---|---|
| 3,929,580 | 12/1975 | Forgione | 435/17 |
| 3,933,592 | 1/1976 | Clendenning | 435/17 |
| 4,001,088 | 1/1977 | Antonik | 435/17 |
| 4,067,775 | 1/1978 | Wuezburg | 435/17 |
| 4,080,265 | 3/1978 | Antonik | 435/8 |

OTHER PUBLICATIONS

"Determination of Creatine Kinase Isoenzyme MB Activity in Serum Using Immunological Inhibition of Creative Kinase", Subunt Activity, Neumier Climica Chimica Acta 73 (1976) 445-451.
"Immobilized Firefly Luciferase", Lee, Analytical Biochemistry 80, (1977), pp. 490-501.

Primary Examiner—Ernest G. Therkorn
Attorney, Agent, or Firm—Fisher, Christen & Sabol

[57] ABSTRACT

A method for the photometric determination of the subunit B of creatine kinase (CK-B) in buffered water solution through reaction with creatine phosphate, ADP and the system luciferase/D-luciferin in the presence of a specific antibody inhibiting the subunit M of creatine kinase, comprises making the determination in the presence of a D-luciferin analog, such as L-luciferin, having a structure similar to D-luciferin and being a competitive inhibitor of the firefly luciferase reaction.

Also disclosed is a reagent for carrying out the above method comprising creatine-phosphate, ADP, luciferase, D-luciferin, L-luciferin, CK-M inhibiting antibodies, diadenosinpentaphosphate, SH-reagent, magnesium salt and buffer as well as possibly stabilizers and/or complex forming reagent.

9 Claims, 1 Drawing Figure

METHOD FOR PHOTOMETRIC DETERMINATION OF THE SUBUNIT B OF CREATINE KINASE AND A REAGENT FOR CARRYING OUT THE METHOD

The present invention refers to a method for photometric determination of the subunit B of creatine kinase (CK-B) especially in serum, and a reagent suitable for carrying out the method.

The creatine kinase enzyme (EC 2.7.3.2) catalyses the transformation

Creatine phosphate + ADP ⇌ Creatine + ATP.

In human tissue there exist two different subunits of this enzyme, namely M and B. The active enzymatic unit always consists of two subunits which together could form three different isoenzymes, namely the muscular type (CK-MM), the brain type (CK-BB) and the hybrid type (CK-MB) which in practice only appears in myocardial tissue. However, at a heart infarction the hybrid enzyme CK-MB appears also in serum. This isoenzyme CK-MB is therefore of great importance in the diagnosis of acute myocardial infarction.

From Clinica Chimica Acta 73 (1976), pp 445 to 451 there is known a method for determining the isoenzyme CK-MB, which eventually is based on determination of the subunit CK-B. This is possible as the brain enzyme CK-BB which always contains the subunit CK-B does normally not appear in serum and thus consequently the CK-B activity found in serum is derived from the isoenzyme CK-MB. In the method known per se the determination takes place by determining the ATP obtained in accordance with the above cited reaction in accordance with the following equation:

$$ATP + D\text{-Glucose} \underset{}{\overset{\text{Hexokinase}}{\rightleftarrows}} ADP + D\text{-Glucose-6-phosphate}$$

$$D\text{-Glucose-6-phosphate} + NADP \underset{}{\overset{\text{G6P-DH}}{\rightleftarrows}} D\text{-Gluconolacton-6-phosphate} + NADPH$$

The determination is specific for CK-MB as it takes place in the presence of antibodies which specifically inhibit the activity of the subunit M of the creatine kinase(CK-M).

An essential disadvantage of the method known per se is firstly a too low sensitivity and secondly, the method includes a delay phase which is dependant on temperature and which is not possible to reduce to less than 90 seconds. This delay phase has the consequence that when the method is used in automatic analysers their capacity cannot be fully used and in certain fast analysers the method cannot be used at all. Furthermore, the concentrations of CK-B in serum at a heart infarction is very low and because of the low sensitivity of the method known per se the activity appearing cannot be determined with the required accuracy.

It is an object of the present invention to provide a method for determining the subunit B in creatine kinase in which the above mentioned disadvantages are eliminated. Thus, the method according to the invention does not suffer from the lag phase and the sensitivity is considerably increased in comparison with the method known per se and furthermore, as the reaction is linear it makes a kinetic measuring possible.

According to the invention the above object is achieved by means of a method for photometric determination of the subunit B of creatine kinase CK-B in buffered water solution by means of reaction with creatine phosphate, ADP and the system luciferase/D-luciferin in the presence of a specific antibody inhibiting the subunit M of the creatine kinase, the method being characterized by that the determination is carried out in the presence of a D-luciferin analog, such as L-luciferin, having a structure similar to D-luciferin and being a competitive inhibitor of the firefly luciferase reaction.

A method for determining creatine kinase (not subunit B) by using luciferase-D-luciferin-systems is known per se. (Analytical Biochemistry 80, (1977) pp 496–501). This method uses purified luciferase together with D-luciferin, ADP, creatine-phosphate, magnesium sulphate and buffer. The light emission will however thereby appear as a peak which complicates the practical use of the method and makes kinetic determinations impossible. Only through the combination of the method and the antibody inhibiting the subunit M and the addition of L-luciferin it is possible to determine the subunit B and simultaneously obtain a continuous light emission proportional to the enzyme activity of the subunit B which makes a kinetic monitoring of the light emission possible. It was not foreseeable that in the presence of M subunit inhibiting antibodies the luciferase reaction would be quantitative, nor was it foreseeable that it was possible to transform the peak light emission to continuous emission extending for several minutes and thereby simultaneously eliminate the lag phase.

Luciferase is obtained from the American firefly (Photinus pyralis) and is possible to purify by methods known per se. According to the invention the luciferase substance of the highest possible purity is used as unpurified luciferase substances contain interfering substances. Luciferase catalyses the reaction Luciferin + ATP + $O_2$ → Oxyluciferin + $CO_2$ + AMP + PPi + Light The amount of light emitted is directly proportional to the ATP-concentration.

In the method according to the invention luciferase is suitably used in concentrations between 0.5 and 20 μg/ml, preferably in quantities between 1 and 3 μg/ml, these amounts referring to the pure luciferase. As to the D-luciferin the amount in the test solution is suitably between 25 and 500 μg/ml, preferably between 50 and 150 μg/ml.

In accordance with the preferred embodiment of the invention diadenosinpentaphosphate is added in amounts in the order of $5 \times 10^{-8}$ to $5 \times 10^{-6}$ M. Any remaining residual disturbances from the myokinase are negligible particularly at low concentrations of ADP. The ADP concentration is usually between $1 \times 10^{-5}$ and $5 \times 10^{-3}$ M, preferably between $1 \times 10^{-5}$ and $5 \times 10^{-4}$ M.

L-luciferin is preferably added in such an amount that at least a 25% inhibition of the luciferase reaction is obtained. The inhibition should however not be above 95%. Preferably the amount added is such that an inhibition between 50 and 90% is obtained. The above suggested preferred ranges for the addition of luciferase and D-luciferin gives an addition of L-luciferin suitably in the order of 1 to 10 μg/ml.

Additionally, a suitable magnesium salt, such as magnesium acetate, is added. An addition of further stabilizing means for enzymes, such as bovine serum albumin and/or complex generating reagents, such as EDTA, is possible.

The type of buffer used is not critical. Suitable buffers are for instance imidazol-acetate-buffer, Tris-acetate-buffer, triethanolamin-acetate-buffer or phosphate-buffer. Preferably, Imidazol-acetate-buffer is used. The pH determined by the buffer should be in the order of 6.5 to 7.8, preferably from 6.7 to 7.0. The buffer concentration could be varied within wide ranges. Thus, a concentration from 10 to 250 mM could be used. Preferably 60 to 120 mM is used.

Suitably a thiol protecting reagent is added to the reaction solution, such as N-acetyl cystein (NAC), Gluthathion, Ditriotreitol or dithioerythrit. Preferably NAC is used. The preferred concentration range for this reagent is between 2 and 50 mM.

A creatine phosphate is added in excess. A preferable range is 5 to 50 mM, preferably 8 to 15 mM.

A further object of the invention is to provide a reagent for determining the subunit B of creatine kinase, comprising creatine phosphate, ADP, luciferase, D-luciferin, L-luciferin, CK-M specific antibodies, diadenosinpentaphosphate, SH-reagent, magnesium salt and buffer as well as stablisers and/or complex forming reagents.

The complex forming reagent to be used according to the invention is for instance ethylendiamintetra acetic acid (EDTA) and Nitrilotriacetic acid.

Suitably the reagent comprises in a lyophilisated or with water recomposed form, the above defined components in the following quantities.

TABLE

|  | preferred quantity | suitable quantity |
| --- | --- | --- |
| Creatine-phosphate | 8–15 mM | 5–50 mM |
| ADP | $1 \times 10^{-5}$–$5 \times 10^{-4}$M | $1 \times 10^{-5}$–$2 \times 10^{-3}$M |
| Luciferase | 1–3 µg/ml | 0.5–20 µg/ml |
| D-luciferin | 50–150 µg/ml | 25–500 µg/ml |
| L-luciferin | 1–10 µg/ml | 0.5–20 µg/ml |
| CK-M-Antikorper[(+)] |  |  |
| Diadenosinpentaphosphate | $1 \times 10^{-7}$–$1 \times 10^{-6}$M | $5 \times 10^{-8}$–$5 \times 10^{-6}$M |
| Thiolreagent | 2–50 mM | 1–100 mM |
| Magnesiumacetate | 5–20 mM | 1–100 mM |
| Imidazol acetate buffer and possibly | 60–120 mM | 10–250 mM |
| Bovine serum albumin | 0.5–2 g/l | 0.1–10 g/l |
| EDTA | 0.5–10 mM | 1–5 mM |

[(+)]sufficient to inhibit completely a CK-MM-activity of 1000 U/1 sample solution at 25° C.

The reagent can be supplied containing all its constituents or can be supplied as a test kit as several separate solutions containing different constituents. If the mixture contains all the constituents, the reaction starts by adding the sample solution to be determined, preferably a serum sample. If a preincubation with a serum sample is required at least one of the constituents necessary for the reaction for instance ADP and/or creatine phosphate are added only at the end of the incubation period.

By means of the method and reagent according to the invention it is possible to carry out the determination of the subunit B of creatine kinase with considerably higher sensitivity as compared to the method known per se. As the lag phase is eliminated the method is more suited for automatic analysis equipment. The determination of the subunit M would easily be carried out in the same way, however without adding the antibodies specifically inhibiting the subunit M whereafter the total activity of the creatine kinase is determined and the activity of the subunit B determined according to the invention is subtracted from the total activity.

Antibodies specifically inhibiting subunit M of creatine kinase are known per se. Such antibodies are obtained through immunisation of test animals suitably goats with the isoenzyme CK-MM and extracting the antibody containing fraction from the serum. A method for extracting these antibodies is described for instance in Clinica Chimica Acta 73, (1976) p 446.

The following examples explain the invention in detail.

EXAMPLE 1

| Solutions | Concentration in the solution | End concentration in the test |
| --- | --- | --- |
| (a) Luciferase reagent |  |  |
| pure luciferase | 10 µg/ml | 2 µg/ml |
| D-luciferin | 250 µg/ml | 50 µg/ml |
| L-luciferin | 20 µg/ml | 4 µg/ml |
| Bovine serum albumin (BSA) | 5 mg/ml | 1 mg/ml |
| Magnesium acetate | 50 mM | 10 mM |
| (b) Buffer |  |  |
| Imidazolacetate | 143 mM | 100 mM |
| EDTA | 2.9 mM | 2 mM |
| N-acetyl cystein (NAC) | 14.3 mM | 10 mM |
| (c) ADP-reagent |  |  |
| ADP | $5 \times 10^{-4}$ M | $10^{-5}$ M |
| Ap$_5$A | $5 \times 10^{-6}$ M | $10^{-7}$ M |
| Imidazolacetate | 100 mM | 100 mM |
| (d) Creatine phosphate | 0.5 M | 10 mM |
| (e) ATP-standard-solution | $10^{-5}$M | $2 \times 10^{-7}$ m |

Test Instructions

Constituants mixed:
0.2 ml luciferase reagent
0.7 ml buffer
10 to 50 µl serum-sample
20 µl CK-M-antibody solution
After 15 minutes incubation at 25° C. is added:
20 µl ADP-reagent and
20 µl creatine-phosphate-solution.

The increase of the light emission is monitored by a commercially available monitor and a printer. The rise is determined. Thereafter a 20 µl ATP-solution is added as an internal standard. The obtained rise of the signal is used as a calibration.

FIG. 1 of the attached drawing shows the typical development with respect to time of the light signal obtained.

EXAMPLE 2

To prepare a reagent according to the invention 2 mg luciferase, 5 mg D-luciferin, 400 µg L-luciferin, 100 mg bovine serum albumin 1 m mol magnesium acetate, 10 m mol Imidazol-acetate, pH 6.7, 0.2 m mol EDTA, 1 m mol N-acetylcystein, $10^{-6}$ mol ADP, $10^{-8}$ mol diadenosinpentaphosphate and 1 m mol creatine phosphate are solved in 94 ml water and lyophilisised.

To reconstituate the reagent before use is solved again in 94 ml water. The amount of reagent is sufficient for carrying out 100 tests. The reagent is initially determined by addition of the creatine kinase comprising serum sample.

EXAMPLE 3

Testkit: for 100 tests

I. Luciferase reagent

Lyophilisate is solved in 20 ml water and comprises:

2 mg luciferase
5 mg D-luciferin
400 µg L-luciferin
100 mg bovine serum albumin
1 m mol Magnesium acetate

II. Buffer

Lyophilisate is solved in 70 ml water and comprises:

10 m mol Imidazol acetate, pH 6.7
0.2 m mol EDTA
1 m mol N-acetyl cystein
2 ml CK-M-antibody solution

III. ADP-reagent

Lyophilisate dissolved in 2 ml water comprises:

$10^{-6}$ mol ADP
$10^{-8}$ mol Ap$_5$A
200 m mol Imidazol acetate, pH 6.7

IV. Creatine phosphate

Lyophilisate dissolved in 2 ml water comprises:

1 m mol creatine phosphate

This test-kit enables a preincubation to be carried out with the sample to be determined. The determination then follows example 1 above adding the corresponding amounts of the solvents III and IV.

I claim:

1. Method for photometric determination of the subunit B of creatine kinase (CK-B) in buffered water solution through reaction with creatine phosphate, ADP and the system luciferase/D-luciferin in the presence of a specific antibody inhibiting the subunit M of creatine kinase, characterized in that the determination is made in the presence of a D-luciferin analog having a structure similar to D-luciferin and being a competitive inhibitor of the firefly luciferase reaction.

2. Method according to claim 1, characterized in that diadenosinpentaphosphate is added.

3. Method according to claims 1 or 2, characterized in that ADP in a quantity of $10^{-5}$ to $5 \times 10^{-3}$ M is added.

4. Method according to claim 1, characterized in that the method is carried out at a pH value between 6.5 and 7.8.

5. Method according to claim 4, characterized in that a buffer concentration between 10 mM and 250 mM is used.

6. Method according to claim 1, characterized in that a thiol protecting reagent, preferably N-acetylcystein, glutathion, dithiotreitol or dithioerythrit, is added.

7. Reagent for carrying out a method for the photometric determination of the subunit B of creatine Kinase (CK-B), comprising creatine-phosphate, ADP, luciferase, D-luciferin, L-luciferin, CK-M inhibiting antibodies, diadenosinpentaphosphate, SH-reagent, magnesium salt and buffer.

8. Reagent according to claim 7, characterized in that it comprises:

| | |
|---|---|
| 5 to 50 mM | Creatine phosphate |
| $1 \times 10^{-5}$ to $5 \times 10^{-3}$ M | ADP |
| 0.5 to 20 µg/ml | Luciferase |
| 25 to 500 µg/ml | D-luciferin |
| 0.5 to 20 µg/ml | L-luciferin |
| | CK-antibodies |
| $5 \times 10^{-8}$ to $5 \times 10^{-6}$ M | diadenosinpentaphosphate |
| 1 to 100 mM | Thiolreagent |
| 1 to 100 mM | magnesiumacetate |
| 10 to 250 mM | Imidazol-acetate-buffer |

9. Reagent according to claim 8, characterized in that it comprises:

| | |
|---|---|
| 8 to 15 mM | creatine phosphate |
| $1 \times 10^{-5}$ to $5 \times 10^{-4}$ M | ADP |
| 1 to 3 µg/ml | Luciferase |
| 50 to 150 µg/ml | D-luciferin |
| 1 to 10 µg/ml | L-luciferin |
| | CK-antibodies |
| $1 \times 10^{-7}$ to $1 \times 10^{-6}$ M | Diadenosinpentaphosphate |
| 2 to 50 mM | Thiol reagent |
| 5 to 20 mM | magnesium acetate |
| 60 to 120 mM | Imidazol-acetate-buffer |

* * * * *